United States Patent [19]

Jacobson

[11] Patent Number: 5,591,890
[45] Date of Patent: Jan. 7, 1997

[54] PROCESS FOR PRODUCING ORTHO-NITRO AROMATIC ACIDS BY OXIDATION OF ORTHO-NITROALKYLAROMATIC COMPOUNDS

[75] Inventor: Stephen E. Jacobson, Princeton Junction, N.J.

[73] Assignee: E. I. Du Pont de Nemours and Company, Wilmington, Del.

[21] Appl. No.: 552,420

[22] Filed: Nov. 3, 1995

[51] Int. Cl.$^6$ .................................................. C07C 51/16
[52] U.S. Cl. ............................................ 562/412; 562/414
[58] Field of Search .................................... 562/412, 414

[56] References Cited

U.S. PATENT DOCUMENTS

| | | |
|---|---|---|
| 2,673,217 | 3/1954 | Hull . |
| 4,007,223 | 2/1977 | Feld .................................... 562/414 |
| 4,603,220 | 7/1986 | Feld .................................... 562/416 |
| 4,906,771 | 3/1990 | Young .................................. 562/416 |

OTHER PUBLICATIONS

M. G. Scaros and M. L. Prunier, Catalysis of Organic Reactions, *Marcel Dekker, Inc*, 314, 1995.
Ryoichi Hasegawa and Yoshio Kamiya, Studies on the Liquid Phase Oxidation of Nitroalkylbenzenes Catalyzed by Transition Metal and Bromide Ions, *Bulletin Chem. Soc. Jap.*, 51 (5), 1490–1494, 1978.

*Primary Examiner*—Michael L. Shippen
*Attorney, Agent, or Firm*—George A. Frank

[57] ABSTRACT

A process for preparing o-nitroaromatic acids by direct oxidation of the corresponding o-nitroalkylaromatic compounds, utilizing salts of certain catalytic metals in the presence of an oxygen-containing gas and an aliphatic aldehyde or ketone at elevated temperature and pressure, is provided. The process allows catalyst recovery and reuse.

5 Claims, No Drawings

PROCESS FOR PRODUCING ORTHO-NITRO AROMATIC ACIDS BY OXIDATION OF ORTHO-NITROALKYLAROMATIC COMPOUNDS

FIELD OF THE INVENTION

The invention relates to a process for the preparation of ortho-nitroaromatic acids (ONAA) by the direct oxidation of ortho-nitroalkylaromatic compounds (ONAC), using molecular oxygen and a metal catalyst.

BACKGROUND OF THE INVENTION

Ortho-nitroaromatic acids are used in many applications, for example, as intermediates in dyes, pharmaceuticals and agrochemicals. Ortho-nitrobenzoic acid is used as a corrosion inhibitor. Anthranilic acid (2-aminobenzoic acid) can be prepared by hydrogenation of o-nitrobenzoic acid. Anthranilic acid is used as an intermediate in the manufacture of dyes, pharmaceuticals, pigments, perfumes and flavors and as an antioxidant.

It is well documented in the literature that ONAC show great resistance to direct oxidation compared with meta- or para- nitroalkylaromatic compounds. This was reported by Hasegawa et al, Bulletin Chem. Soc. Jap., 51 (5), 1490 (1978), based on a study of the liquid phase autoxidation of nitroalkybenzenes catalyzed by a transition metal and bromide ions in acetic acid. More recently Partenheimer, Catalysis of Organic Reactions, Pub. Marcel Dekker, Inc. 1995, p. 314 stated, "m- and p- nitrotoluene can be smoothly oxidized to the nitrobenzoic acids in high yield, while o-nitrotoluene is completely inert." In U.S. Pat. No. 4,906,771, Young et al. state that "It has been known while meta and para- nitrotoluene are readily oxidized, by means of molecular oxygen in the presence of bromine and a heavy metal oxidation catalyst, to the corresponding nitrobenzoic acid the ortho isomer, namely o-nitrotoluene, is unexpectedly resistant to oxidation by this process. Similarly, other o-nitroalkylaromatics, such as 2-nitro-paraxylene, are unexpectedly resistant to oxidation." Young et al. were able to obtain 50 to 90 mole % yields of ortho-nitrobenzoic acid by the direct oxidation of a mixture of ortho-nitrotoluene and an equivalent amount of a co-oxidizable compound, such as toluene or para-xylene at 120° C. to 220° C. and 150 psig and 400 psig. This process suffers from the disadvantages of requiring by-product separation steps, decreased reactor capacity for the production of the desired ortho-nitrobenzoic acids, permitting no catalyst recycle and requiring the use of corrosion resistant equipment made from expensive alloys.

Hull, U.S. Pat. No. 2,673,217. describes a process for the selective oxidation of alkylaromatic compounds using aldehyde-activated catalysts, by first preparing a catalyst solution which is "activated" by simultaneously adding an aliphatic aldehyde and an oxygen-containing gas, and thereafter feeding the alkylaromatic compounds, together with an excess of oxygen, into the catalyst solution while maintaining the catalyst in the solution in an active state by continuously adding aldehyde. The oxidation is conducted at low temperatures (between 50° C. and 90° C.) and pressures (usually atmospheric pressure). Only meta and para-nitroalkyl aromatic compounds are described as substrates and yields of the corresponding aromatic acids are low, between 20% and 37%; there is no disclosure of the oxidation of ortho-nitroalkylaromatic compounds.

There is a need for a safe, environmentally acceptable and economically attractive direct oxidation process for the production of ortho-nitroaromatic acids in high yield from orthonitroalkylaromatic compounds.

SUMMARY OF THE INVENTION

This invention relates to a process for producing an ortho-nitroaromatic acid by the direct oxidation of an ortho-nitroalkyl aromatic compound having the formula

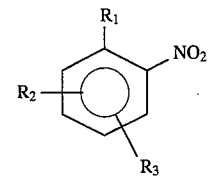

wherein $R_1$ is an alkyl group of 1–4 carbon atoms but not t-butyl; $R_2$ and $R_3$ are H, $R_1$, $CO_2H$, $SO_3Na$, $SO_2R_1$, F, Cl, Br and $NO_2$, can be in any other available position in the aromatic ring and can be the same or different, comprising the steps of:

A. adding to a pressure vessel said ortho-nitroalkyl aromatic compound, oxidation resistant solvent and a salt of a catalytic metal soluble in said solvent;

B. raising the temperature and pressure of the contents to above 90° C. up to 150° C. and between 10.5 bar and 70 bar, respectively, by heating and introducing an oxygen-containing gas;

C. introducing an aliphatic aldehyde or ketone;

D. maintaining the contents in presence of a continuous supply of said oxygen-containing gas and said aliphatic aldehyde or ketone until at least 50% conversion of said ortho-nitroalkylaromatic compound to the corresponding acid is accomplished;

E. recovering the catalyst by the addition of an alkali metal carbonate to the contents followed by a separation step; and F. recovering the product ortho-nitroaromatic acid by acidification and separation.

DETAILED DESCRIPTION OF THE INVENTION

Many ortho-nitroalkylaromatic compounds can be oxidized to the corresponding ortho-nitroaromatic acids by the process of this invention. Provided a nitro group is in the ortho position relative to an alkyl group which is oxidized to a carboxylic acid group, other aromatic ring substituents can also be present. The process can also be used for the oxidation of ONAC derivatives containing one or more electron with drawing substituent groups, such as sulfone. The addition of a basic salt in such cases greatly enhances the yield of desired product.

The ortho-nitroalkylaromatic compounds that can be used in the process have the following formula:

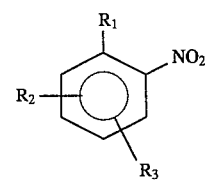

and are oxidized to ortho-nitroaromatic acids having the following formula;

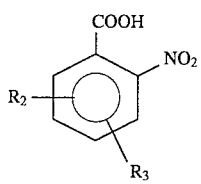

wherein $R_1$ is an alkyl group of 1–4 carbon atoms but not t-butyl; $R_2$ and $R_3$ are optional substituents that can be in any other available position in the aromatic ring and which can be the same or different including H, $R_1$, $CO_2H$, $SO_3Na$, $SO_2R_1$, F, Cl, Br and $NO_2$. Desired products are ortho-nitrobenzoic acid (ONBA), 2-nitro-4-methyl sulfonyl benzoic acid (NMSBA) and 2-nitro-5-fluorobenzoic acid (NFBA).

Catalysts suitable in this process include metal cations such as cobalt (II), cobalt (III), manganese(II), manganese(III), iron (II), iron (III) and zirconium (IV). The metals are added as salts that are soluble in the solvent used. Examples of suitable salts include acetate, propionate, butyrate, carbonate, oxide and hydroxide. Most commonly a single metal compound is used and from the standpoint of availability, solubility, efficiency and ease of recycling cobalt (II) acetate is preferred. Mixtures of the metal catalysts can also be used in this process.

Electron withdrawing substituent groups in the ortho-nitroalkylaromatic compounds, such as sulfonyl substituents, can have an adverse effect on the catalytic process. It has been discovered that, when this is the case, the addition of a basic salt has a beneficial effect enhancing the yield of desired product. Basic salts such as acetate, carbonate and hydroxide of lithium, sodium, potassium, magnesium and calcium can be used in the process of this invention. Mixtures of basic salts can be used but usually a single salt is used. Sodium acetate is preferred as it is readily available and inexpensive.

The process of this invention is carried out in an oxidation resistant medium in which the reactants are soluble or suspended, preferably the former because this favors a more uniform and faster reaction and facilitates recovery of the catalyst and ONAA. Aliphatic carboxylic acids are particularly suitable solvents for the process of this invention, for example, acetic, propionic, burytic, valeric acid and the like. Mixtures of such acids can also be used. Also suitable are mixtures of carboxylic acids and other oxidation resistant organic solvents such as acetic anhydride, o-dichlorobenzene and chlorobenzene. The acids or mixtures can be diluted with water. Acetic acid is a preferred solvent for reasons of economy, availability and environmental acceptability.

Air is the preferred form of oxygen-containing gas and is continuously supplied to the reactants, although enrichment of the oxygen content can be done to expedite the process.

An aliphatic aldehyde or ketone is also supplied continuously throughout the reaction. Among suitable aldehydes are acetaldehyde, propionaldehyde, paraldehyde, metaldehyde, methyl ethyl ketone and their mixtures. This component is preferably introduced as a liquid or in solution in the solvent used in the reactor or in an another oxidation resistant solvent which is miscible with the reaction medium. Acetaldehyde is preferred because of its availability and low cost.

The process can be carried out in a well-stirred pressure vessel to which the solvent and reaction components are first added. It is an advantage of this process compared with many prior art processes that the reactants and catalyst are not corrosive so that equipment made from conventional low cost materials, such as stainless steel, can be used.

The following ranges of concentrations of the components are given as weight percent based on the total charge to the reactor, the preferred ranges being those which result in the most economical operation of the process in relation to the highest conversion of ONAC and highest yield of the desired ONAA.

The initial charge of ONAC can be between 3% to 50% and typically between 5% to 30%. Catalyst metal cation concentration can be between 0.01% to 5% and typically between 0.1% to 3%. The molar ratio of ONAC substrate to catalyst can be between 2:1 to 100:1 and typically between 4:1 to 30:1. When basic salt is added, the amount can be between 0.5% to 20% and typically between 1% to 10%, and the molar ratio of basic salt to catalyst can be between 0.3:1 to 30:1 and typically between 1:1 to 20:1. The balance of the charge to the reactor can be solvent which can contain up to 3% water.

The reactor is pressurized with gaseous oxidant, typically air, flowing continuously throughout the reaction to between 10.5 bar and 70 bar. The mixture is heated above 90° C. and up to 150° C., typically above 90° C. and up to 120° C. The continuous addition of an aldehyde or ketone, usually below the surface of the reactants, is then begun and maintained throughout the reaction by means of a suitable high precision monitoring pump. In the case of a one liter pressure vessel, a suitable air input rate can be between 0.1 to 5 standard liters per minute (slpm), typically 1 to 3 slpm. Depending on the catalyst concentration, the aldehyde or ketone addition rate can be between 0.02 to 2 mole/hour (M/hr), typically 0.1 to 1 M/hr.

The reaction conditions are maintained until at least 50% conversion of ONAC is accomplished, 2 to 12 hours usually being sufficient. By conversion is meant mole % ONAC reacted. The reaction mixture can then be cooled and vented to atmospheric pressure. When the oxygen is depleted, the catalyst metal cation can be reduced to a lower valence state by the addition of an aldehyde, such as paraldehyde. The solvent can then be removed under vacuum and sufficient aqueous alkali metal carbonate, about 15% concentration, is added with stirring at about 50° C. to bring the pH above 8.5. This precipitates the catalyst metal cation as the carbonate and extracts the product ONAA into aqueous solution as its alkali metal salt. The metal carbonate can be removed by filtration and the filter cake can be re-used as a catalyst. The filtrate is acidified, typically to a pH of about 1, using a mineral acid such as 10% HCl, to precipitate the ONAA which can be recovered by filtration and dried in a vacuum oven at a moderate temperature, such as 50° C. Any unreacted ONAC which is immiscible with the filtrate can be separated and recycled.

In the following examples "conversion" is mole % of ONAC reacted, "selectivity" is defined as:

$$\frac{\text{moles ONAA produced}}{\text{moles ONAC reacted}} \times 100\%, \text{ and}$$

yield is the percentage of product recovered based on the quantity of staffing material.

EXAMPLES

Example 1

Preparation of ortho-Nitrobenzoic acid (ONBA) by Oxidation of ortho-Nitrotoluene (ONT)

A one-liter stainless steel autoclave reactor fitted with a stirrer, a dip tube and gas inlet and outlet couplings was charged with 90.4 g ONT (0.66 mole, Fluka Co., 99% purity), 29.0 g cobalt (II) acetate tetrahydrate (0.12 mole, Baker Analyzed Reagent, 100.2% assay), 8.2 g water and 384 g glacial acetic acid. The mixture was stirred and pressurized to 62 bar with air continuously flowing at one slpm and then heated to 100° C. The addition of 100% acetaldehyde (Fluka Co.>99.5% assay) to the stirred mixture subsurface via a dip tube was then begun at a continuous flow of 0.27 g/min with a high pressure, precision, single piston, positive displacement pump (Model 500 ISCO syringe pump). At the end of six hours the reaction mixture was cooled to room temperature and the pressure was vented to atmospheric pressure. Analysis by liquid chromatography (LC) showed an 88% conversion of ONT and a 100% selectivity to ONBA.

Example 2

Preparation of ONBA by Oxidation of ONT and Catalyst Recycle

A one-liter autoclave as described in Example 1 was charged with ONT (57.6 g, 0.42 mole), cobalt (II) acetate tetrahydrate (5.2 g, 0.021 mole), water (1.9 g), ortho-dichlorobenzene (3.2 g, internal standard) and acetic acid (384 g). The mixture was stirred and pressurized to 24.1 bar with air continuously flowing at 2 slpm and then heated to 100° C. Acetaldehyde was then added at the rate of 0.71 cc per minute, subsurface via a dip tube. The reaction was run under these conditions for four hours, then cooled to 70° C. and air was replaced with nitrogen. Acetaldehyde was introduced at 0.71 cc per minute for three minutes and the mixture was stirred under nitrogen for o three hours to reduce Co(III) to Co(II). Analysis by LC showed 6.1% ONBA and 2.8% ONT remaining (69.6% conversion, 78.2% selectivity). Acetic acid was then removed from the reaction mixture under vacuum and sodium carbonate (106.5 g, 15%) was then added under agitation until pH=9 was reached. The resulting insoluble cobalt carbonate was filtered out. The filtrate was titrated with 10% HCl to pH=1, and the resulting insoluble ONBA was recovered by filtration (33.7 g, 48% yield).

The filter cake cobalt(II) carbonate (11.1 g) from above was added to ONT (57.6 g), water (1.9 g), and acetic acid (384 g), and the resulting mixture was reacted under the same conditions as above. The Co(III) to Co(II) reduction was also carried out as above. Analysis by LC showed 7.1% ONBA and 2.3% ONT remaining (75.5% conversion, 81.6% selectivity). Cobalt (II) carbonate was recovered as filter cake and ONBA isolated as above (40 g, 56.9% yield).

The filter cake cobalt(II) carbonate (12.6 g) from the first recycle was again added to ONT (57.6 g), water (1.9 g), and acetic acid (384 g), and the resulting mixture was reacted under the same conditions as above. Analysis by LC showed 6.9% ONBA and 2.5% ONT remaining (72.5% conversion, 86.3% selectivity).

These latter two reactions demonstrate the effective recovery and reusability of the catalyst of this invention.

Examples 3–6

Preparation of ONBA by Oxidation of ONT

In Examples 3,4 and 6 the procedure of Example 1 was used. Example 4 is a comparative example in which temperature and pressure were below the lower limits of the process of this invention. Example 5 is a comparative example wherein the procedure, temperature and pressure were according to U.S. Pat. No. 2,673,217. The results and reaction parameters are summarized in Table 1 and show that, surprisingly, much higher conversion and selectivity were obtained using the process and conditions of this invention (Examples 3 and 6) when compared to the two comparative examples (Examples 4 and 5).

TABLE 1

Oxidation of ONT

| Ex. | ONT gram | ONT mole | Catalyst gram | Catalyst mole | $H_2O$ gram | Temp. °C. |
|---|---|---|---|---|---|---|
| 3 | 57.6 | 0.42 | 5.2 | 0.021 | 1.9 | 112 |
| 4 | 57.6 | 0.42 | 5.2 | 0.021 | 1.9 | 90 |
| 5 | (1) |  | 5.2 | 0.021 | 1.9 | 90 |
| 6 | 76.8 | 0.56 | 34.9 | 0.14 | 10.6 | 100 |

| Ex. | Air bar | Air slpm | Aldehyde cc/min. | Reaction Time (hr.) | Reaction conv % | Reaction selec % |
|---|---|---|---|---|---|---|
| 3 | 24.1 | 2 | 0.71 | 4 | 90.3 | 80.2 |
| 4 | 10.3 | 1 | 0.46 | 4 | 34.6 | 63.6 |
| 5 | 10.3 | 1 | 0.66(1) | 4 | 24.5 | 59.0 |
| 6 | 36.9 | 1 | 0.71 | 3 | 95.2 | 97.7 |

(1)61:39 acetaldehyde:ONT mixture, continuously added.

Example 7

Preparation of 2-Nitro-4-methylsulfonyl benzoic acid (NMSBA) by Oxidation of 2-Nitro-4-methylsulfonyl toluene (NMST)

A one liter autoclave, as described in Example 1, was charged with NMST (>97% purity; 22.4 g, 0.10 mole), 4.4 g water, cobalt(II) acetate tetrahydrate (6.2 g, 0.025 mole), sodium acetate trihydrate (8.2 g, 0.06 mole), and 384 g acetic acid. The stirred mixture was pressurized to 62 bar with continuously flowing air at 2 slpm and then heated to 100° C. The addition of a 50:50 mixture of acetic acid and acetaldehyde was then begun at a continuous flow of 0.6 g/min using a precision high pressure pump, as described in Example 1. At the end of four hours the reaction mixture was vented to atmospheric pressure. LC analysis showed 3.9 wt % NMSBA and 0.05% NMST remaining (98.7% conversion, 88.6% selectivity).

The mixture was then reacted with paraldehyde (4 g, 0.03 mole, Sigma Chemical Co.) at 70° C. for two hours to reduce Co(III) to Co(II). Acetic acid was then removed under vacuum to dryness. Aqueous sodium carbonate (15%, 75 g, 0.19 mole) was then added and the mixture was stirred at 50° C. (pH=8.7). The solution was then filtered to remove the cobalt(II) carbonate and any unreacted starting material. The filtrate was titrated with 10% HCl to pH=1 and the resulting 2-nitro-4-methylsulfonyl benzoic acid was removed by filtration and dried at 50° C. in a vacuum oven (17.4 g, 68.8% yield,>99% pure).

Example 8

Preparation of 2-Nitro-5- fluorobenzoic acid (NFBA) by Oxidation of 2-Nitro-5-fluorotoluene (NFT)

A one-liter autoclave, as described in Example 1, was charged with NFT (57.6 g, 0.37 mole, Aldrich Chemical Co., 97% purity), cobalt (II) acetate tetrahydrate (4.6 g, 0.019 mole), water (1.9 g) and acetic acid (384 g). The stirred mixture was pressurized to 24.1 bar with continuously flowing air at 2 slpm and heated to 112° C. 100% acetaldehyde was introduced and its flow maintained at 0.71 cc per minute. After eight hours the reaction mixture was cooled to room temperature and the pressure was vented to atmospheric pressure. LC analysis showed 6.4 wt % NFBA and 0.80 wt % NFT remaining (89.3% conversion and 80.0% selectivity).

I claim:

1. A process for producing an ortho-nitroaromatic acid by the direct oxidation of an ortho-nitroalkyl aromatic compound having the formula

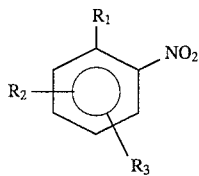

wherein $R_1$ is an alkyl group of 1–4 carbon atoms but not t-butyl; $R_2$ and $R_3$ are H, $R_1$, $CO_2H$, $SO_3Na$, $SO_2R_1$, F, Cl, Br and $NO_2$, can be in any other available position in the aromatic ring and can be the same or different comprising the steps of:

A. adding to a pressure vessel said ortho-nitroalkylaromatic compound, oxidation resistant solvent and a salt of a catalytic metal soluble in said solvent;

B. raising the temperature and pressure of the contents to above 90° C. up to 150° C. and between 10.5 bar and 70 bar, respectively, by heating and introducing an oxygen-containing gas;

C. introducing an aliphatic aldehyde or ketone;

D. maintaining the contents in presence of a continuous supply of said oxygen-containing gas and said aliphatic aldehyde or ketone until at least 50% of said ortho-nitroalkylaromatic compound is converted to the corresponding acid;

E. recovering the catalyst by the addition of an alkali metal carbonate to the contents followed by a separation step; and F. recovering the product ortho-nitroaromatic acid by acidification and separation.

2. The process of claim 1 wherein $R_2$ and $R_3$ are electron withdrawing groups and wherein a basic salt is also added to said pressure vessel.

3. The process of claim 1 wherein the salt of catalytic metal is selected from the group consisting of acetate, propionate, butyrate, carbonate, oxide and hydroxide of cobalt (II), cobalt (III), manganese(II), manganese(III), iron (II), iron (III) and zirconium(IV).

4. The process of claim 1 wherein the concentration of ortho-nitroalkylaromatic compound is 3%–50%, the concentration of the metal catalyst is 0.01%–5%, and the molar ratio of the ortho-nitroalkylaromatic compound to catalyst is from 2:1 to 100:1.

5. The process of claim 2 wherein the concentration of ortho-nitroalkylaromatic compound is 3%–50%, the concentration of the metal catalyst is 0.01%–5%, the molar ratio of the ortho-nitroalkylaromatic compound to catalyst is from 2:1 to 100:1 and the concentration of said basic salt is 0.5%–20%.

* * * * *